US00PP36049P2

(12) United States Plant Patent
Danziger

(10) Patent No.: US PP36,049 P2
(45) Date of Patent: Jul. 30, 2024

(54) ***PETUNIA* PLANT NAMED 'DPETAMPLUC'**

(50) Latin Name: ***Petunia* Juss.**
Varietal Denomination: DPETAMPLUC

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 18/243,845

(22) Filed: Sep. 8, 2023

(51) Int. Cl.
*A01H 5/02* (2018.01)
*A01H 6/82* (2018.01)

(52) U.S. Cl.
USPC ..... Plt./356.13

(58) Field of Classification Search
USPC ..... Plt./356.13

CPC . A01H 5/02; A01H 5/00; A01H 6/824; A01H 6/82
See application file for complete search history.

(56) References Cited

PUBLICATIONS

Danziger Amazonas Plum Cockatoo retrieved on Nov. 15, 2023 at at https://www.danzigeronline.com/catalog/annuals/amazonas-plum-cockatoo/, 2 pp. (Year: 2023).*
Growers Talk California Spring Trials Day 4; Takii, HilverdaFlorist, Danziger, Syngenta 2023 retrieved on Nov. 15, 2023 at https://www.growertalks.com/Newsletters/View/?article=4147, 18 pp. (Year: 2023).*

* cited by examiner

*Primary Examiner* — June Hwu
(74) *Attorney, Agent, or Firm* — Cassandra Bright

(57) ABSTRACT

A new and distinct *Petunia* plant named 'DPETAMPLUC' is disclosed, characterized by distinctive purple, white, and green flowers with good longevity. Plants have a mounded habit, and bright green foliage. The new variety is a *Petunia*, normally produced as an outdoor garden or container plant.

2 Drawing Sheets

Latin name of the genus and species: *Petunia* Juss.
Variety denomination: 'DPETAMPLUC'.

BACKGROUND OF THE INVENTION

The new *Petunia* cultivar is a product of a planned breeding program conducted by the inventor, Gavriel Danziger in Moshav Mishmar Hashiva, Israel. The objective of the breeding program was to produce new *Petunia* varieties for ornamental purposes. The crossing resulting in this new variety was made in a population of unnamed *Petunia* Juss. The date of the crossing is unknown.

The new variety was discovered in April 2020 by the inventor in a group of seedlings resulting from the crossing, in a greenhouse in Moshav Mishmar Hashiva, Israel.

Asexual reproduction of the new cultivar 'DPETAMPLUC' was first performed by terminal vegetative cuttings during August of 2020, at a greenhouse in Moshav Mishmar Hashiva, Israel. Subsequent propagation by vegetative cuttings has shown that the unique features of this cultivar are stable and reproduced true to type in more than 6 successive generations.

SUMMARY OF THE INVENTION

The cultivar 'DPETAMPLUC' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DPETAMPLUC' These characteristics in combination distinguish 'DPETAMPLUC' as a new and distinct *Petunia* cultivar:

1. Unique flower color of green with a dark purple throat and white margin.
2. Good flower longevity.
3. Curly flowers.

PARENT COMPARISONS

Plants of the new cultivar 'DPETAMPLUC' cannot be compared with the parent varieties, as they are unknown.

COMMERCIAL COMPARISONS

Plants of the new cultivar 'DPETAMPLUC' can be compared to the commercial variety *Petunia* 'DCASPITAYA', U.S. Plant Pat. No. 27,999. These varieties are similar in most horticultural characteristics; however, 'DPETAMPLUC' differs in the following:

1. Growth habit of the new variety is mounded, while the growth habit of this comparator is trailing.
2. Flowering of the comparison variety is sensitive for short day length, while the new variety is not.
3. Flower color of the new variety is green, white and purple, while the flower color of this comparator is pink and green.

Plants of the new cultivar 'DPETAMPLUC' can also be compared to the unpatented commercial variety *Petunia* 'Ray Pistachio Cream'. These varieties are similar in most horticultural characteristics; however, 'DPETAMPLUC' differs in the following:

1. Growth habit of the new variety is mounded, while the growth habit of this comparator is upright.
2. Flowers of the new variety are wide open, while flowers of this comparator are more conical.

BRIEF DESCRIPTION OF THE PHOTOGRAPHS

Figure 1:
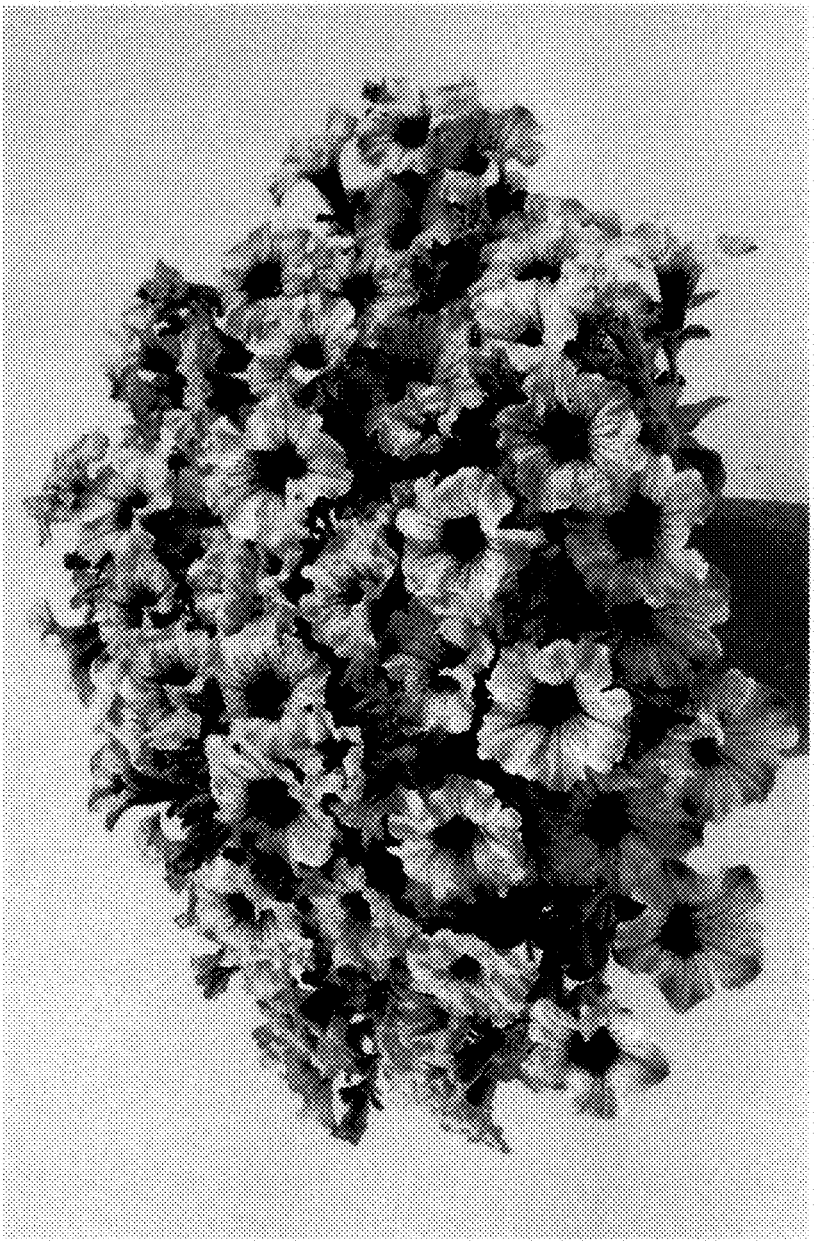

The accompanying photograph in FIG. 1 illustrates in full color a typical plant of 'DPETAMPLUC' grown in a 12 cm pot in Moshav Mishmar Hashiva, Israel under moderate Fall conditions.

Figure 2:
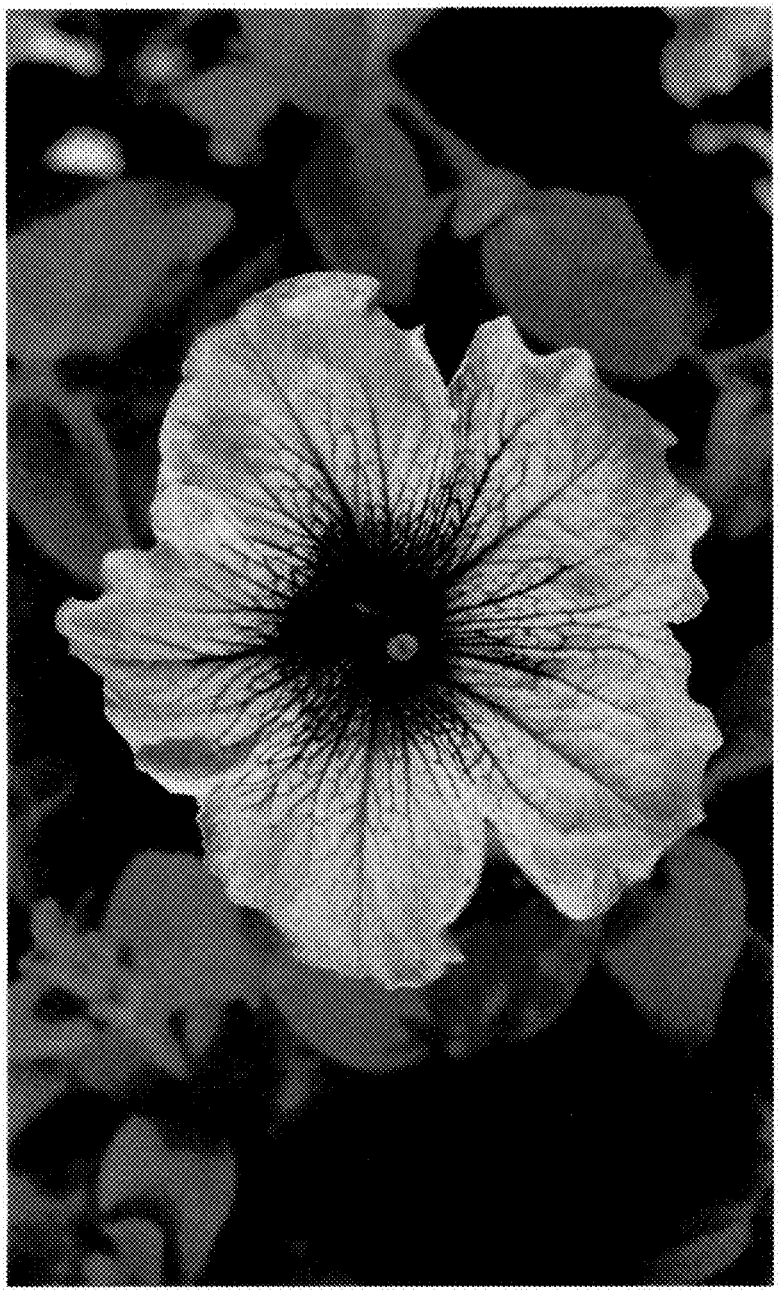

FIG. 2 illustrates in full color a close up view of a typical flower of 'DPETAMPLUC' grown under the same moderate Fall conditions.

Age of the plant photographed is approximately 3 months from a rooted cutting in a 12 cm pot. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DPETAMPLUC' plants grown in a greenhouse in Moshav Mishmar Hashiva, Israel, under natural lighting. Measurements were taken during spring, summer, and autumn. The plants were approximately 12 weeks old from a rooted cutting in a 12 cm pot. The growing temperature ranged from approximately 18° C. to 27° C. during the days, 12° C. to 20° C. during the nights. Measurements and numerical values represent averages of typical plant types. Botanical classification: *Petunia* Juss. 'DPETAMPLUC'.

PROPAGATION

Total rooting time: About 7 to 10 days at approximately 20° to 25° C.

Root description: Branched, white in color, not accurately measured with RHS chart.

PLANT

Growth habit: Mounded.
Pot size of plant described: 12 cm.
Height: About 19 cm to top of flowers.
Plant spread: About 35 cm.
Growth rate: Medium.
Branching characteristics: Good branching.
Length of primary lateral branches: 10 to 15 cm.
Diameter of lateral branches: About 0.2 cm.
Quantity of primary lateral branches: 8.
Characteristics of primary lateral branches:
- *Form.*—Cylindrical.
- *Diameter.*—About 0.3 cm.
- *Color.*—RHS Yellow-Green 144B.
- *Texture.*—Pubescent.
- *Strength.*—Good.

Internode length: About 1.5 cm.

FOLIAGE

Leaf:
- *Arrangement.*—Opposite.
- *Quantity.*—Approximately 40 per branch.
- *Average length.*—3 cm.
- *Average width.*—2 cm.
- *Shape of blade.*—Elliptic.
- *Apex.*—Acute.
- *Base.*—Acute.
- *Margin.*—Entire.
- *Texture of top surface.*—Velvety.
- *Texture of bottom surface.*—Pubescent.
- *Angle of attachment.*—90°.
- *Color.*—Young foliage upper side: RHS Green 143A. Young foliage under side: RHS Green 143 C. Mature foliage upper side: RHS Green 143A. Mature foliage under side: RHS 143C.
- *Venation.*—Type: Pinnate. Venation color upper side: RHS Green 143A. Venation color under side: RHS Green 143B.
- *Petiole.*—Length: 0.8 cm. Diameter: 0.4 cm. Color: RHS Yellow-Green 146B. Texture: Velvety.

FLOWER

Bloom period: Spring, summer, and autumn.
Days to flowering from rooted cutting: 35 days.
Inflorescence and flower type and habit: Curly flowers, with green patches on petals.
Rate of flower opening: 2 to 5 days from bud to fully opened flower.
Flower longevity on plant: 10 days.
Approximate quantity of flowers per plant: 25.
Persistent or self-cleaning: Persistent.
Bud:
- *Shape.*—Tubular.
- *Length.*—3.8 cm.
- *Diameter.*—0.7 cm.
- *Color.*—RHS Yellow-Green 144B.

Flower size:
- *Diameter.*—6.6 cm.
- *Flower tube length.*—2 cm.
- *Flower tube diameter at distal end.*—0.5 cm.
- *Flower tube diameter at proximal end.*—1 cm.

Petals:
- *Length from throat.*—3 cm.
- *Width.*—2 cm.
- *Quantity.*—5.
- *Texture.*—Non-pubescent, crepey upper and lower surfaces.
- *Apex.*—Blunt.
- *Margin.*—Entire. Strongly undulate.
- *Lobing.*—Strong.
- *Color.*—When opening: Upper surface: RHS Violet 92A with Yellow-Green 144B blotches along margin. Lower surface: RHS Violet 92C with Yellow-Green 144B blotches along margin. Fully opened: Upper surface: RHS Yellow-Green 144B blotches near petal apex with center Violet N92C fading to 92A towards petal apex. White N155C along margin and fusion of petal lobes. Smaller apical blotch near Yellow-Green 144C often present within 144B blotch. Very conspicuous venation near N92A. Lower surface: RHS Yellow-Green 144B blotches near petal apex with center Violet 92A. Flower throat (inside): RHS Violet N92D. Flower throat, vein: RHS Violet N92C. Flower tube (outside): RHS Yellow-Green 144B flushed N92A. Flower tube, vein: RHS Violet N92C. Fading: RHS Purple 85D.

Calyx/sepals:

*Quantity per flower.*—5.

*Shape.*—Linear.

*Length.*—About 1.5 cm.

*Width.*—About 0.2 cm.

*Apex.*—Acute.

*Base.*—Cuneate.

*Margin.*—Entire.

*Texture.*—Velvety.

*Color.*—Upper Surface: RHS Yellow-Green 146A. Lower Surface: RHS Yellow-Green 146B.

Peduncle:

*Length.*—About 2.5 cm.

*Diameter.*—About 0.2 cm.

*Color.*—RHS Yellow-Green 146C.

*Orientation.*—45°.

Fragrance: None.

REPRODUCTIVE ORGANS

Stamens:

*Number.*—5.

*Filament length.*—1 cm.

Anthers:

*Length.*—1 cm.

*Shape.*—Rounded.

*Color.*—RHS Purple 85C.

*Pollen.*—Color: RHS Yellow 160D. Quantity: Abundant.

Pistil:

*Number.*—1.

*Length.*—About 2.2 cm.

*Style.*—Length: About 1.8 cm. Color: RHS Yellow-Green 145A.

*Stigma.*—Shape: Rounded. Color: RHS Yellow-Green 145A. Ovary Color: RHS Green 143C.

OTHER CHARACTERISTICS

Seeds and fruits: About 60 brown, rounded seeds of about 0.5 mm diameter, per one, conical capsule.

Disease/pest resistance: Typical resistance and susceptibility to the normal diseases and pests of *Petunia*. Pests common to *Petunia* include Aphids and thrips. Typical diseases are *Botrytis* and *Pythium*.

Temperature tolerance: Tolerates a range between 5° C. to 40° C.

What is claimed is:

1. A new and distinct cultivar of *Petunia* plant named 'DPETAMPLUC' as herein illustrated and described.

* * * * *